United States Patent
Owen et al.

[19]

[11] Patent Number: 6,063,040

[45] Date of Patent: May 16, 2000

[54] SELF RETRACTING NEEDLE APPARATUS AND METHOD FOR PHLEBOTOMY

[75] Inventors: Charles V. Owen, Highland; David L. Thorne, Kaysville; Gale H. Thorne, Bountiful; Roy L. Barrus, West Bountiful, all of Utah

[73] Assignee: Specialized Health Products, Inc., Bountiful, Utah

[21] Appl. No.: 09/008,036

[22] Filed: Jan. 16, 1998

[51] Int. Cl.[7] .................................................. A61B 5/00

[52] U.S. Cl. ........................ 600/573; 604/163; 604/171; 604/192

[58] Field of Search .................................... 600/573, 576, 600/578; 604/162, 163, 171, 192

[56] References Cited

U.S. PATENT DOCUMENTS

| | | | |
|---|---|---|---|
| 3,587,575 | 6/1971 | Lichenstein | 128/128 |
| 4,676,783 | 6/1987 | Jagger | 604/171 |
| 4,747,831 | 5/1988 | Kulli | 604/110 |
| 4,813,936 | 3/1989 | Schroeder | 604/195 |
| 4,828,548 | 5/1989 | Walter | 604/164 |
| 4,850,374 | 7/1989 | Diaz-Ramos | 128/763 |
| 4,892,525 | 1/1990 | Hermann, Jr. | 604/263 |
| 4,900,307 | 2/1990 | Kulli | 604/110 |
| 4,904,242 | 2/1990 | Kulli | 604/110 |
| 4,909,794 | 3/1990 | Haber | 604/195 |
| 4,927,414 | 5/1990 | Kulli | 604/110 |
| 4,929,241 | 5/1990 | Kulli | 604/263 |
| 4,936,830 | 6/1990 | Verlier | 604/110 |
| 4,946,446 | 8/1990 | Vadher | 604/198 |
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,139,489 | 8/1992 | Hollister | 604/192 |
| 5,147,303 | 9/1992 | Martin | 604/110 |
| 5,154,285 | 10/1992 | Hollister | 206/365 |
| 5,180,370 | 1/1993 | Gillespie | 604/110 |
| 5,188,599 | 2/1993 | Botich | 604/110 |

(List continued on next page.)

FOREIGN PATENT DOCUMENTS 9-28811  2/1997  Japan .

OTHER PUBLICATIONS

Patricia Seremet, "Small Tolland Company Takes Jab at Safety Needle Market," *The Hartford Courant*, Sep. 13, 1995, pp. F1 and F3.

*Primary Examiner*—Cary O'Connor
*Assistant Examiner*—Pamela L. Wingood
*Attorney, Agent, or Firm*—Gale H. Thorne

[57] ABSTRACT

A practical, low cost safety device for phlebotomy. Preparation for operation of the device involves elongating an otherwise shortened-for-transport apparatus to extend a medical assembly and needle from a housing for use in a medical procedure. The act of elongating energizes an energy storing component and cocks a releasable latch. The energy storing component is preferably a vacuum drawing plunger and tube combination. When the medical procedure is complete, distortion of a portion of the housing causes powered retraction of the needle. After retraction, the needle is fully contained, permitting the device to be laid aside without fear of an inadvertent needle stick. The housing comprises a proximal barrel and a distal needle containment section. The barrel comprises a sampling tube stopper piercing cannula. The distal section is disposed in-line, but off-axis from the barrel and comprises an enclosed conduit which communicates with the cannula and with a pathway to the medical needle through the medical needle assembly. Construction of the device requires only three injection molded parts, the housing, a needle hub and a needle cover. Further, as the needle is retracted, communication from the conduit is severed and the pathway to the needle is closed to reduce likelihood of blood spatter. The conduit may be used as a blood flash visualization chamber.

24 Claims, 15 Drawing Sheets

U.S. PATENT DOCUMENTS

| | | | |
|---|---|---|---|
| 5,193,552 | 3/1993 | Columbus et al. | 128/760 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |
| 5,209,739 | 5/1993 | Talslay | 604/195 |
| 5,215,533 | 6/1993 | Robb | 604/195 |
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jroe | 604/110 |
| 5,356,392 | 10/1994 | Firth et al. | 604/198 |
| 5,374,250 | 12/1994 | Dixon | 604/110 |
| 5,403,283 | 4/1995 | Lockwood, Jr. | 604/110 |
| 5,407,436 | 4/1995 | Toft | 604/195 |
| 5,480,385 | 1/1996 | Owen | 604/110 |
| 5,487,734 | 1/1996 | Thorne | 604/195 |
| 5,498,245 | 3/1996 | Whisson | 604/192 |
| 5,531,694 | 7/1996 | Clemens | 604/110 |
| 5,542,927 | 8/1996 | Thorne | 604/110 |
| 5,549,708 | 8/1996 | Thorne | 604/110 |
| 5,562,629 | 10/1996 | Haughton | 604/158 |
| 5,573,510 | 11/1996 | Isaacson | 640/158 |
| 5,616,135 | 4/1997 | Thorne | 604/192 |
| 5,656,031 | 8/1997 | Thorne | 604/110 |
| 5,897,508 | 4/1999 | Konrad | 600/573 |

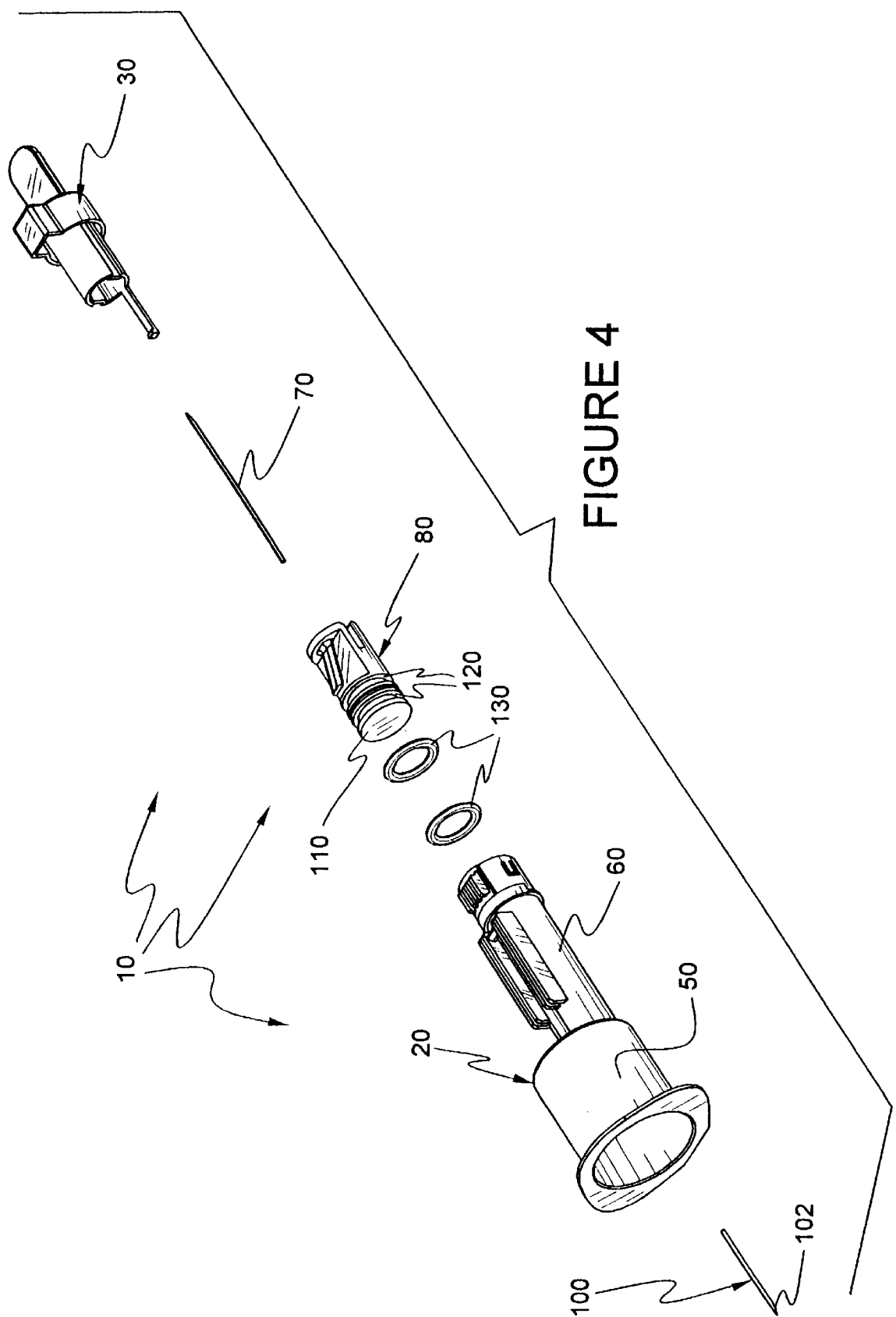

SELF RETRACTING NEEDLE APPARATUS AND METHOD FOR PHLEBOTOMY

FIELD OF THE INVENTION

This invention relates generally to medical needle apparatus and methods and particularly to apparatus comprising medical needles which are self-retracting from an extended position at which the needle is used to a retracted position where the needle is fully withdrawn and encased within a housing for safe disposal. Further, the invention is related to medical products which may only be used once to eliminate cross contamination from one patient to another and to those medical products which have sterile parts inherently protected from contamination without need of additional packaging apparatus.

PRIOR ART

Problems associated with inadvertent needle sticks are well known in the art of blood withdrawal, transdermal medication injection, catheter emplacement and other medical procedures involving uses of medical needles. Ever increasing attention is being paid to needle stick problems due to the contemporary likelihood of being exposed to AIDS and Hepatitis. These problems are particularly evident in the area of phlebotomy.

Commonly, procedures involving withdrawing a standard phlebotomy needle from a patient require a technician to use one hand to place pressure at the wound site where a needle is being withdrawn while removing the needle apparatus with the other hand. It is common practice for a tending clinician to give higher priority to care for the wound than is given to disposal of a needle. Such priority either requires an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for the patient.

Widespread knowledge and history associated with needle care and disposal problems have resulted in conception and disclosure of a large number of devices each of which represents an attempt to provide not only a solution to the problem of needle sticks, but a device which is commercially viable (i.e. cost and price competitive with currently used non-self retracting devices), as well. Though some devices describe application in the area of blood withdrawal (see U.S. Pat. Nos. 4,850,374 (Nydia Diazramos) and 5,195,985 (Hall)), most contemporary related art is directed toward syringes and like devices. U.S. Pat. No. 5,480,385, issued Jan. 2, 1996 to Thorne et al. (Thorne '385), discloses extendable and retractable medical needle apparatus and methods. One linear force storing apparatus associated with needle retraction is disclosed to be an evacuated vacuum chamber. One of the major salient features of one device disclosed in Thorne '385 is a potential reduction in production cost due to opportunity to limit injection modified parts to as few as four parts. Powered medical needle retraction devices are also disclosed in other U.S. Patents and Patent Applications comprising U.S. Pat. No. 5,542,927 issued Aug. 6, 1996, U.S. Pat. No. 5,487,734 issued Jan. 30, 1996, U.S. Pat. No. 5,480,385 issued Jan. 2, 1996, U.S. Pat. No. 5,549,708 issued Aug. 27, 1996, U.S. Pat. No. 5,616,135 issued Apr. 1, 1997, and U.S. Patent application Ser. No. 08/744,108 filed Nov. 5, 1996 entitled Self Retracting Medical Needle Apparatus and Methods for which claims have been granted but the patent, itself, has not yet issued.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary competitive items, those devices are usually not found to be commercially viable. Motivation for providing a cost competitive self-retracting needle apparatus coupled with improved safety of use of the apparatus resulted in conception of the instant inventions disclosed herein.

BRIEF SUMMARY AND OBJECTS OF THE INVENTION

In brief summary, the novel invention disclosed herein dramatically diminishes known major problems resulting from injury-related needle sticks which occur when needle tips are bared as medical needles are withdrawn from a patient at the end of a needle insertion procedure. In preferred embodiments of this novel invention, operation involves elongating an otherwise shortened-for-transport, medical needle apparatus to provide access to a medical needle which is enclosed by a cover or cap prior to use.

The act of elongating the apparatus energizes an energy storing memory element and cocks a releasable latch as a medical needle assembly is displaced. Generally, the needle cover is used as a puller to displace and extend the medical needle assembly. Following displacement, the needle is made available for a medical procedure by physically separating the needle cover from the rest of the apparatus.

In a preferred embodiment, when the medical procedure is complete, simple distortion of a portion of the housing, for example, by squeezing the portion by the thumb and forefinger of one hand, releases energy stored in the memory element which causes the needle to safely retract into the housing. It is important to note that the needle can be retracted directly from a patient and safely encased in the housings by a simple action of a single hand of an attending technician, leaving the technician's other hand free for other concurrent medical procedures, such as care of the wound site from which the needle is retracted. After retraction, the needle is fully enclosed and contained, permitting the needle apparatus to be laid aside without fear of an inadvertent needle stick while full attentive care is provided to the patient.

Generally, then, this novel invention is for a self-retracting medical needle apparatus which is employed in transporting, using and retracting a medical needle into safe containment within a housing after use. The apparatus comprises a housing which further comprises a hollow, elongated cylindrical proximal portion for receiving blood sampling tubes which is proximal to a user during use and a relatively distally disposed hollow, elongated cylindrical segment, the distal segment being in-line, but off-set from the proximal portion.

The proximal portion generally has an open proximal end disposed for receiving fluid sampling tubes and a distally disposed end closed about an axially disposed needle hub. A cannula having a proximally directed sharpened tip, is securely affixed in the needle hub, thereby providing a fluid pathway therethrough to an attached blood sampling tube.

The distal segment comprises an elongated cylinder, closed at a proximal end in the form of a wall which is preferably common with a portion of the closed distal end of the proximal portion. Further, the distal segment comprises a distally disposed opening and an elongated sidewall defining an interior cylindrical surface disposed between the opening and the closed distal end. A unique feature of the housing is found in the off-axis disposition of the distal segment relative to the proximal portion.

Displaceably disposed in the distal cylindric segment is a needle assembly which comprises a hub for a medical needle, a hollow medical needle, and a plunger part comprising at least two slidable seal parts disposed about the hub and aligned transverse to the interior cylindrical surface. The needle assembly is disposed within the distal segment prior to use, partially advanced through the distal opening to extend the medical needle for use in a medical procedure and retracted, by force of energy created by displacing at least one of the seal parts away from the proximal closed end along the interior cylindrical surface creating a vacuum in the energy storing memory element, to power retraction of a medical needle into the distal segment after use. It should be noted that retraction under force of the difference in pressure between ambient atmospheric pressure and the created vacuum is preferred. However, a spring, elastic member or other energy storing element which captures energy through extension of the needle assembly and retracts the medical needle upon activation may be used. Even so, the seal parts, or equivalent, are necessary for routing fluid from the medical needle to a conduit which leads to the cannula.

The hub further comprises a releasable latch and the distal segment comprises a corresponding catch whereby the needle assembly is releasibly affixed when displaced for the medical procedure. To complete a flow path from the medical needle to a fluid sampling tube, the sidewall either comprises or is directly associated with the conduit which is totally enclosed and has an opening at a proximal end for communicating with the fluid pathway and having an opening at a predetermined distal site through the sidewall which communicates with a fluid transmitting space disposed between the two seal parts. The hub further has a fluid communicating recess which delivers fluid from a proximal end of said medical needle into space between the seal parts for delivery into the conduit. In this manner, an interruptible, fixed length, enclosed pathway for fluid is established between the medical needle and the cannula.

Retraction is initiated by distorting a deformable section of the distal segment to communicate with the latch and thereby displace the latch from the catch. As the medical needle is retracted, the fluid transmitting space disposed between the seal parts no longer communicates with the opening in the surface of the sidewall thus sealing the proximal end of the medical needle and hub recess to prevent acceleration of internally disposed fluid relative to the hub and needle and thereby guard against inadvertent spatter from the distal end of a retracting medical needle.

To provide evidence of tampering and a seal against contamination, a removable label is affixed to the open proximal end for detachment immediately prior to use of the apparatus. Likewise the apparatus comprises a cap which provides a sterile barrier, evidence of tampering and denies access to the medical needle until removed. The cap also acts as a puller which is used to extend the medical needle assembly from the distal segment until the medical needle apparatus and needle are displaced for apparatus use. The cap is then removed.

Displacement of the medical needle apparatus energizes the energy storing element. The linear motion energy storage member may be a spring, an elastic tube, a plunger which draws a vacuum in a chamber as the apparatus is extended or any other component which stores retracting energy as the apparatus is elongated. However, the storage member in the preferred embodiment of this invention is a drawn vacuum acting against atmospheric pressure.

It is important to note that a device which is based upon the invention may be fabricated from as few as three injection molded parts, the housing, the medical needle hub and the cover. Other parts which may be used to complete fabrication of the device comprise the medical needle, the seals (seal parts), the proximally disposed cannula and a blood valve which is commonly disposed about proximal cannulae in contemporary blood draw apparatus. Being able to construct the device from so few injection molded parts to form a retractable medical needle instrument and sealing the flow path from the medical needle and hub upon retraction set this invention apart from other devices disclosed in the prior art section, above.

One other feature of the present invention is the opportunity of using the conduit as a blood flash visualization chamber, a feature which is not available on contemporary phlebotomy devices.

Accordingly, it is a primary object to provide a novel and improved medical needle extending and retracting device comprising a housing and associated needle cover which, in combination, protect tip integrity and sterility of a medical needle and other internal parts of the device until use and which fully retracts the needle into the housing after use.

It is a key object to provide a housing part which provides a barrel portion for use with an evacuated blood sampling tube, a needle containment segment from which a medical needle is extended for use and into which the medical needle is retracted after use and a conduit associated with the walls of the housing wherethrough fluid displaced from the medical needle flows into the evacuated tube.

It is another key object to provide a needle cover for the device which is releasibly affixed to the housing during transport and storage of the device, which is a discardable component used to maintain a sterile needle prior to use and to extend the needle for use.

It is an important object to provide a means for releasing a cocked needle assembly for subsequent retraction by distorting a portion of the housing rather than requiring a button or other mechanical device to project through the housing wall.

It is another primary object that the device be usable but once and the needle be safely enclosed when retracted.

It is a very important object that the device be made with as few as three injection molded parts.

It is a significant object to provide a manufacturing method for assembly of the device which is compatible with automatic assembly equipment.

It is an object to provide a force storing memory element which stores energy as the apparatus is extended and which provides needle retracting force upon release of the needle assembly.

It is an object to provide a vacuum producing apparatus in which energy is stored in the form of a vacuum used to produce retracting force upon a needle.

It is an important object to seal one end of the medical needle during retraction to retard spatter from a retracting needle.

These and other objects and features of the present invention will be apparent from the detailed description taken with reference to accompanying drawings.

BRIEF DESCRIPTION OF THE DRAWINGS

FIG. 4 is an exploded perspective of the blood draw device parts except for the proximal label and blood valve.

DETAILED DESCRIPTION OF THE ILLUSTRATED EMBODIMENTS

In this description, unless differently specified, the term proximal is used to indicate the segment of a device normally closest to a user when it is being used. In like manner, the term distal refers to the other end. Reference is now made to the embodiments illustrated in FIGS. 1–17 wherein like numerals are used to designate like parts throughout. Parts which are similar in form and function in previously numbered parts are commonly designated by numbers primed for facile cross-reference.

Figure 1:
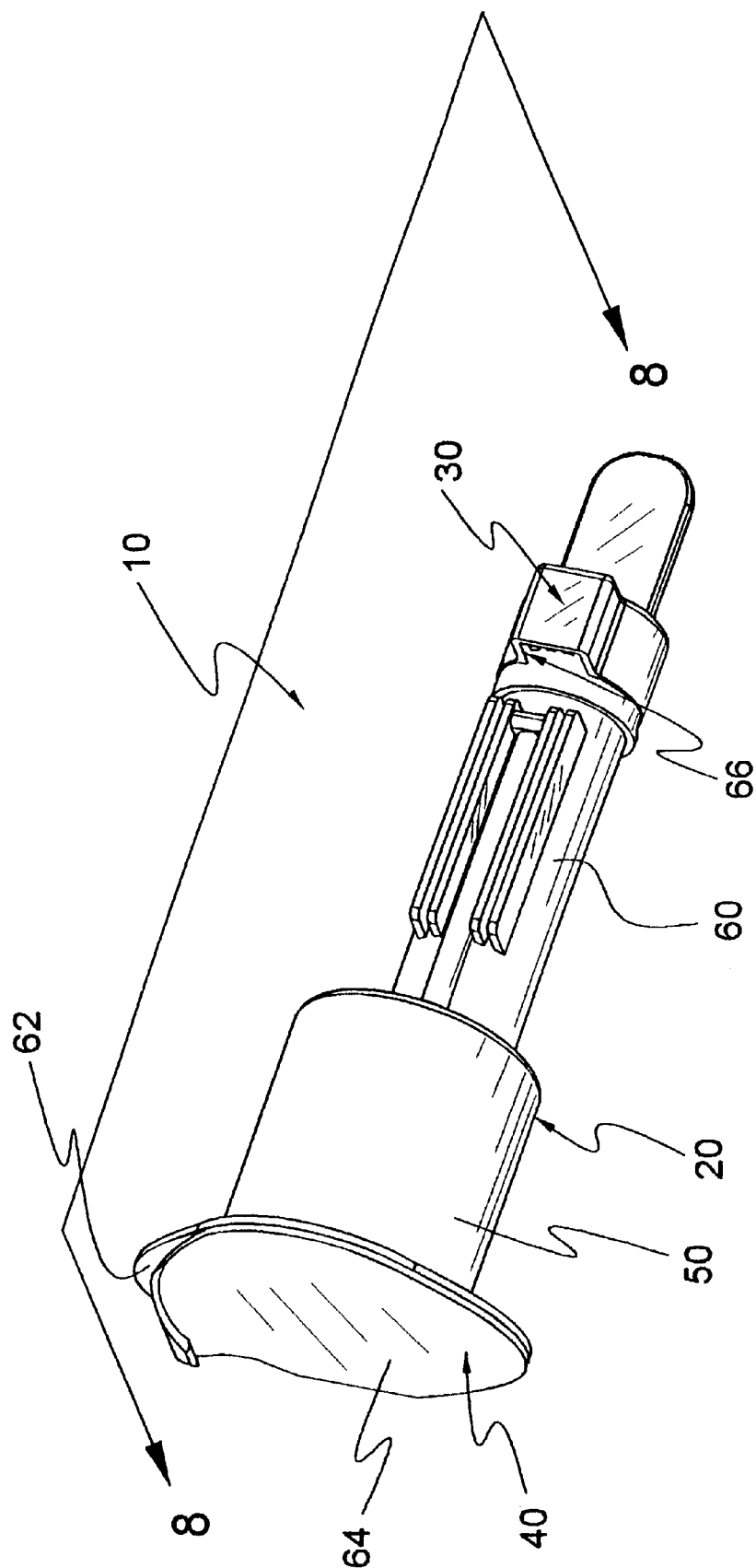
FIG. 1 is a perspective of a sealed blood draw device, showing the exterior of the device housing with a proximal label partially removed.

Reference is now made to FIG. 1 wherein an embodiment of the present invention is seen. This embodiment is a self-contained device 10 which may be transported and stored without a bubble pack or other protective covering and which comprises a housing 20, a distally disposed, removable protective cap 30 and a proximally disposed label-seal 40 Housing 20 comprises a proximal portion 50 and a distal section 60. Proximal portion 50 provides the function and generally has the form of a barrel portion of a commonly used barrel for blood acquisition systems which use evacuated sampling tubes similar to the Becton Dickinson and Company Vacutainer® tube. However, portion 50 comprises a proximally facing surface 62 to which a label 40 is attached (preferably by adhesive or heat seal) to provide a closed back surface 64 and, thereby, protect space internal to the barrel from environmental contamination. The seal also provides positive evidence of tampering when prematurely removed.

Section 60 is a transport container for a needle assembly and medical needle prior to use and a safety housing for the medical needle after use. Section 60 comprises an interface, generally designated by 66, which comprises an environmentally protective tortuous pathway from exterior to interior of section 60.

Figure 2:
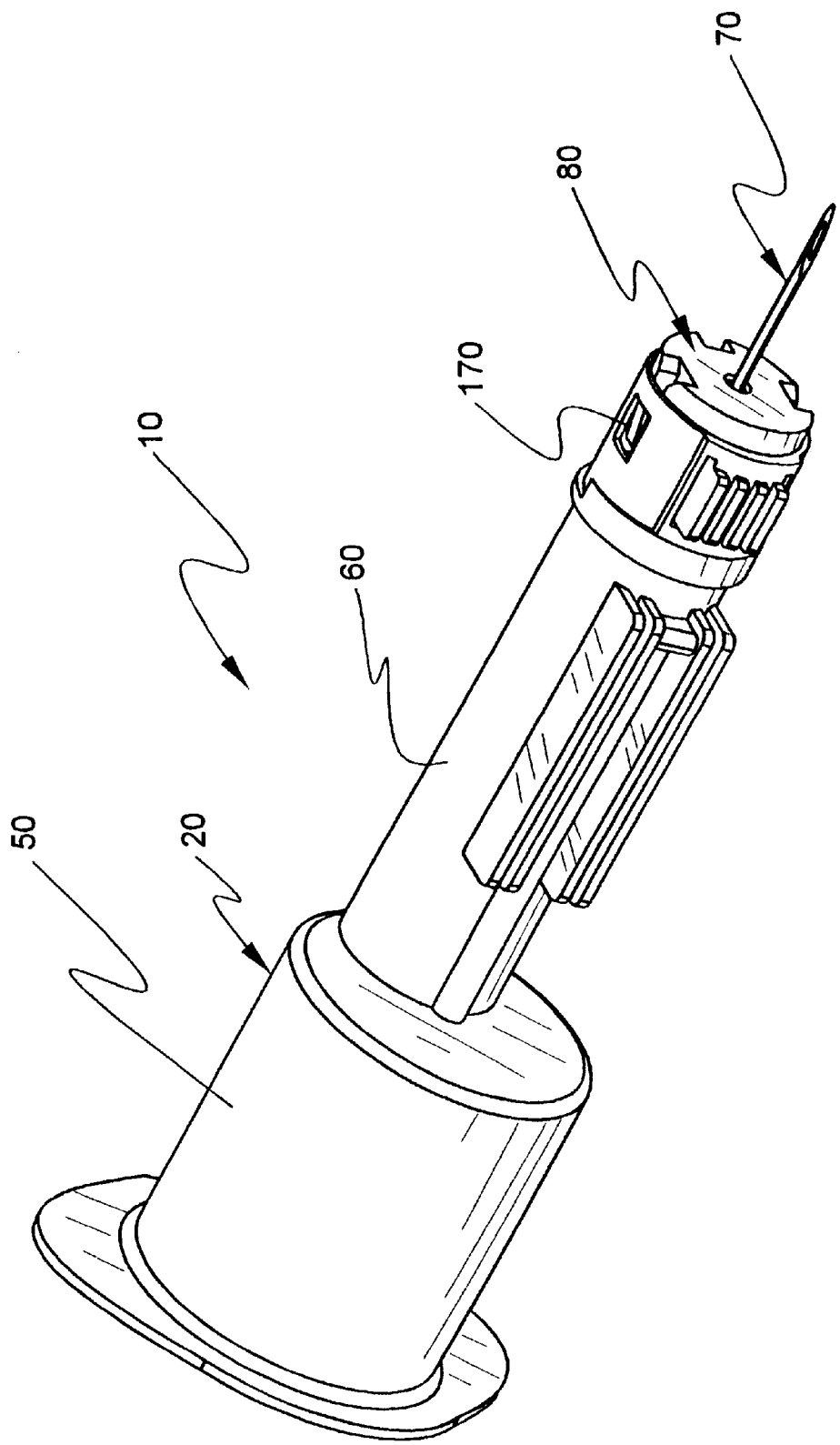
FIG. 2 is a perspective of the device seen in FIG. 1 having proximal label removed, needle cover extracted to bare an extended medical needle for use and rotated approximately 90° for a clear representation of parts unseen in FIG. 1.

To prepare device 10 for use, cap 30 is detached by a linear distal motion baring a phlebotomy needle 70 as seen in FIG. 2. Prior to separation of cap 30, needle 70 is securely, though separably latched to housing 20 by a latch portion of a needle hub 80. The latch portion and other details of hub 80, not seen in FIG. 2, are disclosed in detail hereafter.

Figure 3:
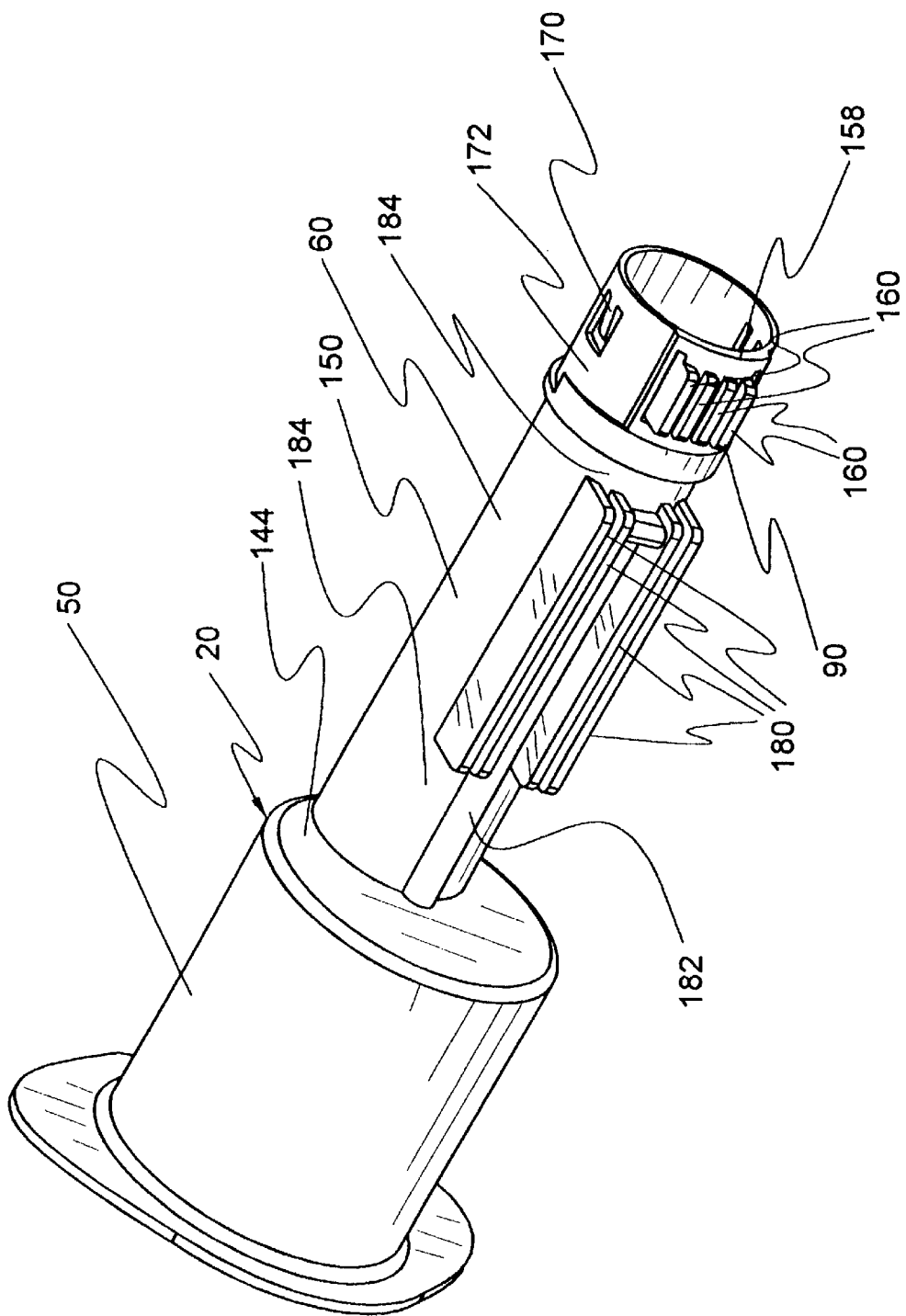
FIG. 3 is a perspective of the device seen in FIG. 1 with the medical needle retracted.

Once the procedure for which device 10 has been prepared and used is complete, needle 70 is automatically retracted into safe enclosure within housing 20, as seen in FIG. 3. Needle retraction is actuated by depressing a distortable trigger 90 conveniently disposed in a superior position on distal section 60.

Reference is now made to FIG. 4, wherein a set of parts of which device 10 is comprised is seen. Of course different parts may be used in place of the parts seen in FIG. 4 within the scope and framework of the instant invention disclosed herein. Even so, this embodiment of device 10 comprises housing 20, cap 30, needle 70 and needle hub 80 as mentioned above. Device 10 further comprises a second needle 100 which is disposed with a proximal needle point 102, normally within proximal barrel portion 50, for piercing a stopper of a blood collection tube. Note that label 40 is not seen in FIG. 4, but should be understood to be an integral part of device 10 until removed in preparation for use in a medical procedure.

A proximal section 110 of hub 80 comprises a series of annular grooves, generally designated 120, for attachment of displaceable seal parts. While other sealing parts may be used within the scope of this invention, a pair of O-rings, each designated 130, are each affixed within a groove 120 to form an airtight nexus. The purpose and function of grooves 120 and seals 130 are disclosed in detail hereafter. Note that device 10 requires but three injection molded parts, and only nine parts overall (not including lubricants and adhesives), including label 40 and a blood valve 42 (seen in FIG. 12). Of the nine parts, needles 70 and 100 are made by materials and methods well known in the medical device art. Labels, blood valves, and o-rings 130 are also commercially attainable; however, care should be taken to select o-rings made of materials which are at least compatible, and preferably inert, with blood and other biological fluids which may be drawn through device 10. As an example, materials currently being used as displaceable plungers in syringes may be employed. The three injection molded parts are preferably made from medical grade polypropylene.

Figure 6:
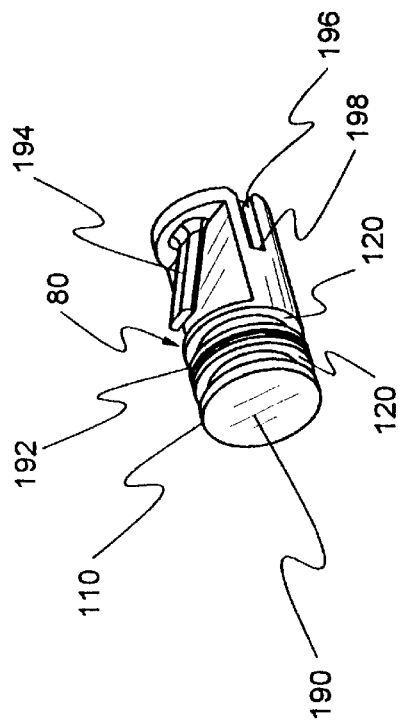
FIG. 6 is a perspective of a needle hub part of the device.
Figure 7:
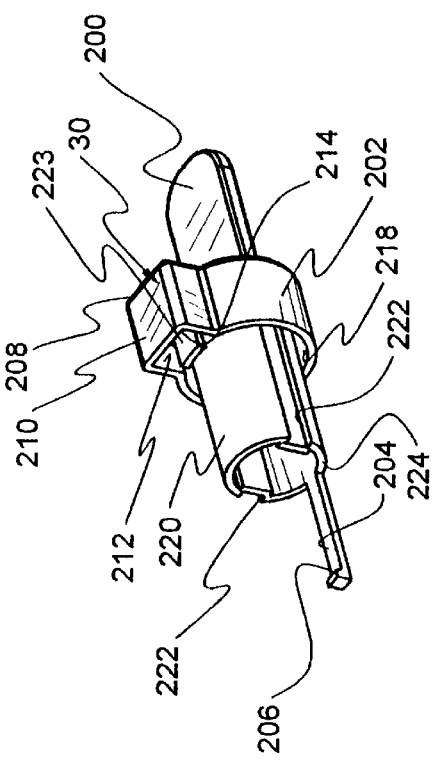
FIG. 7 is a perspective of a cap part of the device.
Figure 5:
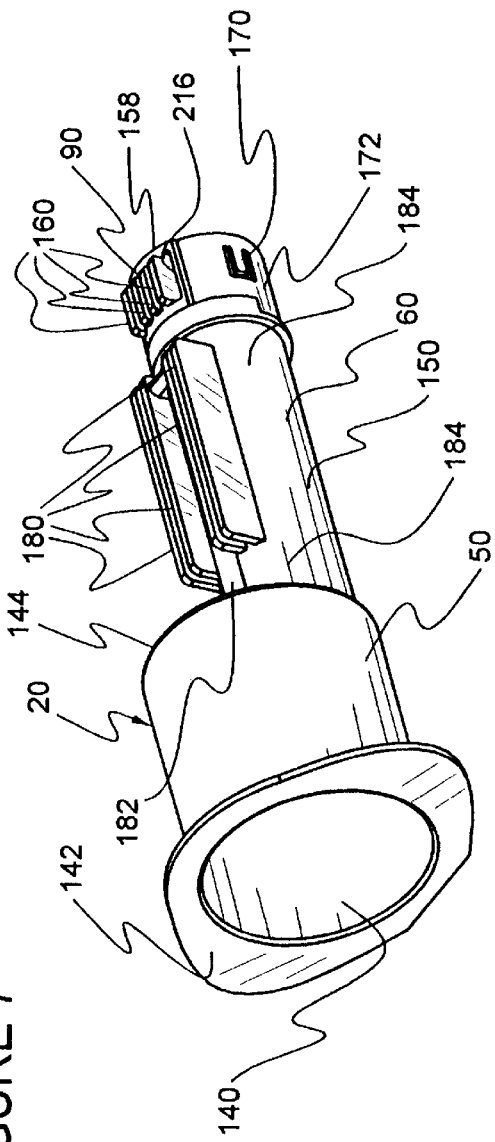
FIG. 5 is a perspective of a housing part of the device.

Reference is now made to FIGS. 5–7 wherein magnified examples of housing 20, hub 80 and cap 30, respectively, are seen. As seen in FIG. 5, proximal barrel portion 50 of housing 20 comprises a hollow, cylindrical core 140 ending abruptly in a planar rim 142, where label 40 is affixed as an environmental barrier and tamper indicator. Cylindrical core 140 is sized to receive evacuated sampling tubes similar to the Becton Dickinson & Company Vacutainer® tubes. As is better seen FIG. 3, barrel portion 50 comprises a truncated and closed distal end 144 which includes but a single fluid pathway 146 (seen in FIGS. 8, 9 and 10) therethrough. Pathway 146 is contiguous with a conduit 148 disposed in distal section 60. The form and function of conduit 148 is disclosed in detail hereafter.

Referring once more to FIGS. 3 and 5, distal section 60 comprises a substantially hollow, cylindrical structure 150. A cantilevered button 90 (earlier referenced as trigger 90) is distally and superiorly disposed as seen in FIG. 5. Button 90 is preferably cantilevered from a distal, superior edge 158. Button 90 also preferably comprises a plurality of raised ribs 160 which permit easier identification and facile digital access. Also distally disposed in section 60 is at least one distortable tab 170, seen in FIG. 5 (in an as molded state) in line with the neighboring outside surface 172 of section 60. Note that tab 170 is depressed inwardly relative to outside surface 172 in FIG. 3. The function and significance of inwardly depressing tab 170 is disclosed in detail hereafter.

Proximal to button 90, section 60 comprises a plurality of raised ribs 180. In combination, ribs 180 provide a comfortable resting or gripping surface for a thumb or finger during use of device 10. In addition, ribs 180 provide protection for material 182 which is raised relative to the general cylindrical surface 184 of section and which encloses conduit 148 (seen in FIG. 8).

Reference is now made to FIG. 6, in which a magnified perspective of hub 80 is seen. Hub 80 comprises the earlier mentioned grooves 120 in proximal section 110, a closed proximal end 190, a slot for a blood path 192 (not easily discerned in FIG. 6, but more easily comprehended in FIGS. 8–10), a proximally protruding latch leg 194, at least one guide slot 196 and an associated stop 198. In addition, the 80 comprises a slot 199, the form of which is better seen in FIGS. 8–10 and the function of which is disclosed hereafter.

A magnified perspective of cap 30 is seen in FIG. 7. Cap 30 comprises a distally disposed pull tab 200, a shield section 202 and a draw strip 204 and hook 206. Shield section 202 covers openings in the distal section 60 (seen in FIG. 5) and creates, in an interface with distal section 60, a tortuous path which shields and protects needle 70 (not seen in FIGS. 5–7) from contamination.

Shield Section 202 comprises a closed distal surface 208 (best seen in FIG. 8) integral with a substantially hollow irregularly shaped cover 210. Cover 210 comprises an internal surface 212 having a raised superior section 214 which fully covers button 90 and protects an opening 216 (see FIG. 5) disposed about three sides of the button. In addition, a continuing inferiorly disposed portion 218 of interior surface 212 closely conforms to outside surface 172 of distal section 60 as part of the tortuous path.

In addition, shield section 202 comprises an internally disposed hollow central core part 220, distally molded integrally with the end comprising surface 208. Part 220 comprises a guide slot 222 for each tab 170. In the embodiment seen in FIGS. 5–10, two tabs 170 are included. A superiorly disposed raised feature 223 proximally disposed is made to conform as part of the tortuous path with a catch ledge 260 (see FIG. 8) disposed within distal section 60 as disclosed hereafter. Proximally, draw strip 204 and hook 206 are affixed to an inferior proximal edge 224 of part 220. Note that hook 206 is formed by an approximate 90° vertical bend in draw strip 204.

Figure 8:
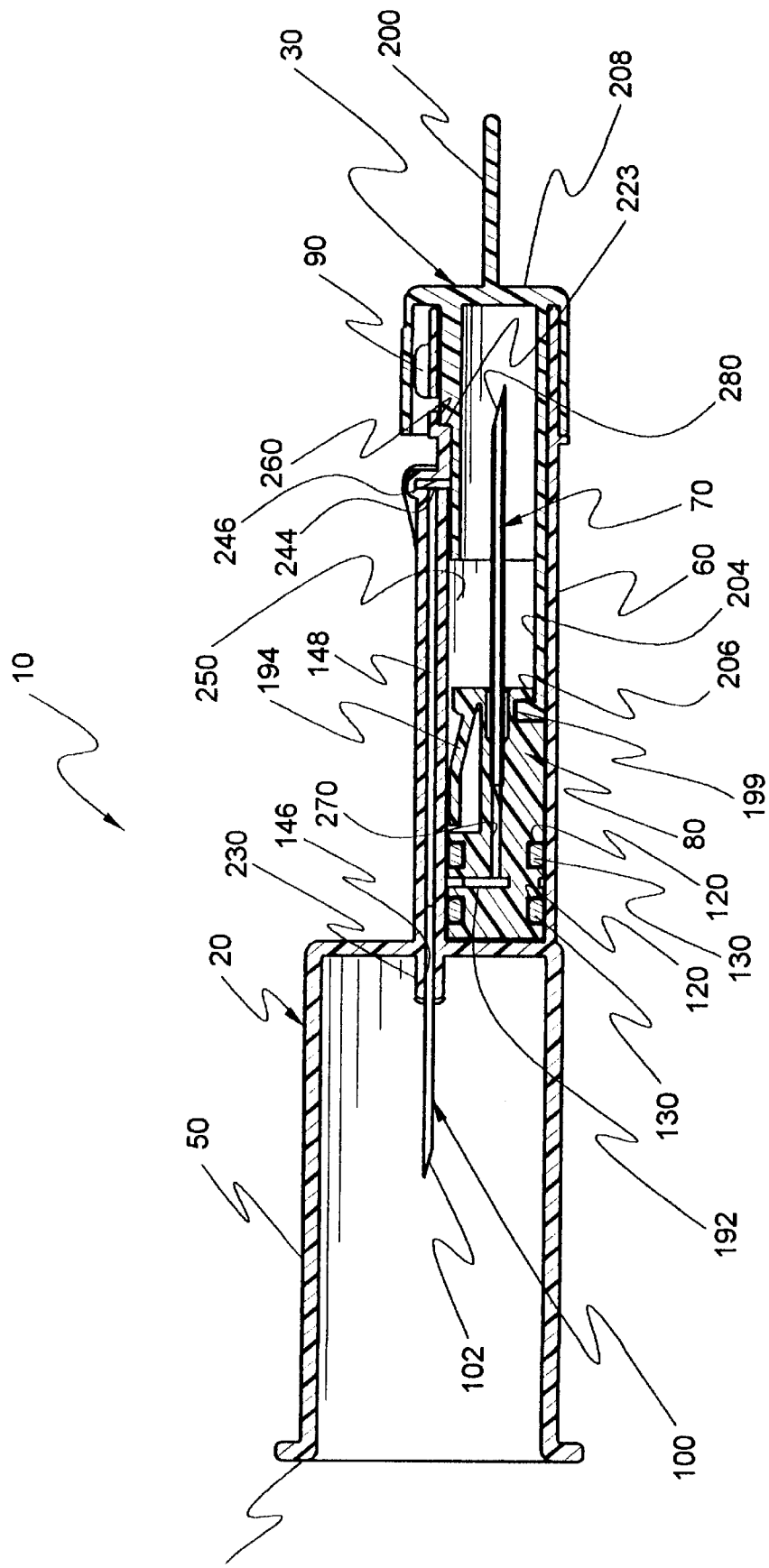
FIG. 8 is a section along lines 8—8 of FIG. 1 after the label has been removed, but before the cap is removed, and shown without a blood valve.

In combination, cap 30 and label 40 provide protection for contents of device 10, permitting the device to be transported without protection of an exterior package, such as a bubble pack, prior to extending needle 70 for use in a medical procedure. A sectional view of device 10 with cap 30 in place, but with label 40 removed is seen in FIG. 8. Device 10 is seen with cap 30 and hub 80 disposed as shipped in conjunction with distal section 60.

As seen in FIG. 8, housing 20 is preferably made of a single injection molded part. Barrel portion 50 comprises a centrally disposed needle hub 230 in which a hollow-bore, rear needle 100 is securely affixed. Rear needle 100 comprises a proximally disposed sharpened end 102, used to provide trans-stopper access to a evacuated sampling tube (not shown). End 102 is preferably ground to a sharp, but non-coring point.

Conduit 148 is disposed in alignment with needle 100 to provide a continuous flowpath thereto. At a distal end 244 of conduit 148, the flowpath continues through a vertical duct 246, which is disposed at a predetermined place whereat a fluid-flow orifice is provided through inner surface 250 of distal section 60.

Distal from duct 246, inner surface 250 comprises catch ledge 260 which interfaces with raised feature 223 of cap 30. Note that o-rings 130 are nested in grooves 120 wherein each o-ring 130 in combination with each respective groove 120 and in subsequent combination with inner surface 250 forms a displaceable fluid-tight seal. Note also that slot 192 is disposed between the two groove 120 and seal 130 combinations.

A fluid pathway is formed from slot 192 to a channel 270 which communicates with hollow-bore, medical needle 70. Medical needle 70 comprises a sharpened tip 280 which should be protected from causing an inadvertent stick both prior to and after a medical procedure.

Hook 206 is disposed in slot 199 and biased against inner surface 250 such that cap 30 is connected to hub 80 until draw strip 204 and hook 206 are free of distal section 60 when hub 80 and needle 70 are extended for use. Cap 30 provides closure of all openings in distal section 60 before being pulled and acts as a puller for hub 80 and needle 70.

Figure 9:
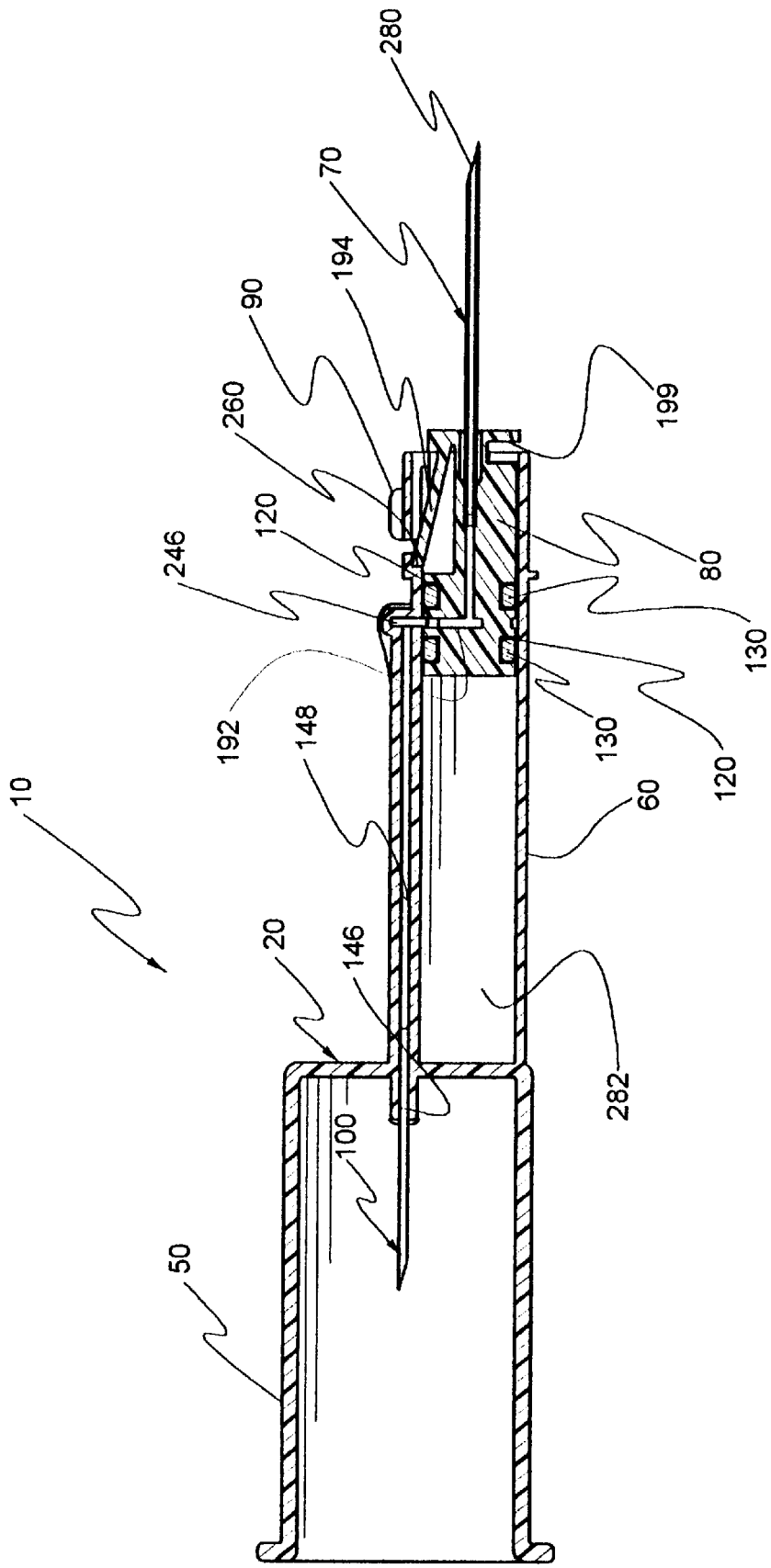
FIG. 9 is a section of the device seen in FIG. 8 with the cap pulled and extracted from the housing and the medical needle extended and latched in place.

As seen in FIG. 9, hub 80 has been pulled distally (using cap 30) until slot 199 is sufficiently disposed outside distal section 60 to free hook 206 and therefore cap 30, which is no longer affixed as a part of device 10. Distal travel of cap 30 is maintained in alignment with hub 80 (i.e. hook 206) is retained within slot 199 by guiding properties of tab 170 constrained in one or more aligned series of guide slots 196 and 222, of hub 80 and cap 30, respectively.

Distal travel of hub 80 is limited by at least one indented tab 170 inwardly bent after hub 80 is inserted into distal section 60 during device 10 assembly. Note that each tab 170 is molded to be flush with inner surface 250. After hub 80 is disposed inside distal section 60, tab 170 is permanently deformed to act as a stop and prevent hub 80 from being pulled from section 60 along with cap 30.

As hub 80 is moved distally, a plunger formed by the combination of the proximal o-ring 130 and proximal groove 120 creates a vacuum in the proximal portion 282 of distal section 60, thereby storing energy which provides a return force for subsequent powered retraction of hub 80 and needle 70. At the point where hub 80 collides with inwardly distorted tab 170 (best seen in FIG. 10), latch leg 194 superiorly disposed to be releasibly affixed against catch ledge 260 to act as a stop against inadvertent retraction of hub 80 and needle 70.

When latch leg 194 is disposed against catch ledge 260, slot 192 communicates with duct 246 to form a continuous fluid pathway from the bore of needle 70 through slot 192 to conduit 148 and finally to proximal needle 100. Note that the long axis of needle 70 is offset from the long axis of needle 100. This offset requires a non-linear fluid path between the needles, but permits needle 70 to be disposed in an inferior location relative to needle 100, thereby permitting a shallow percutaneous entry angle. Further, the transverse orientation of the pathway comprising slot 192 and duct 148 permits the slot 192/duct 148 pathway to be broken as hub 80 and needle 70 are retracted.

Simple depression of button 90 (distortion of a portion of housing 20) releases latch leg 194 from catch ledge 260, causing the vacuum (i.e. force of the related pressure differential between ambient air and portion 282) to retract needle 70 and hub 80. It is important to note that the pathway from needle 70 through slot 192 is totally closed as the distal o-ring 130 moves proximally past duct 246 during needle 70/hub 80 retraction. This closure severely restricts spatter of blood which might otherwise be ejected from tip 280 during retraction.

Figure 10:
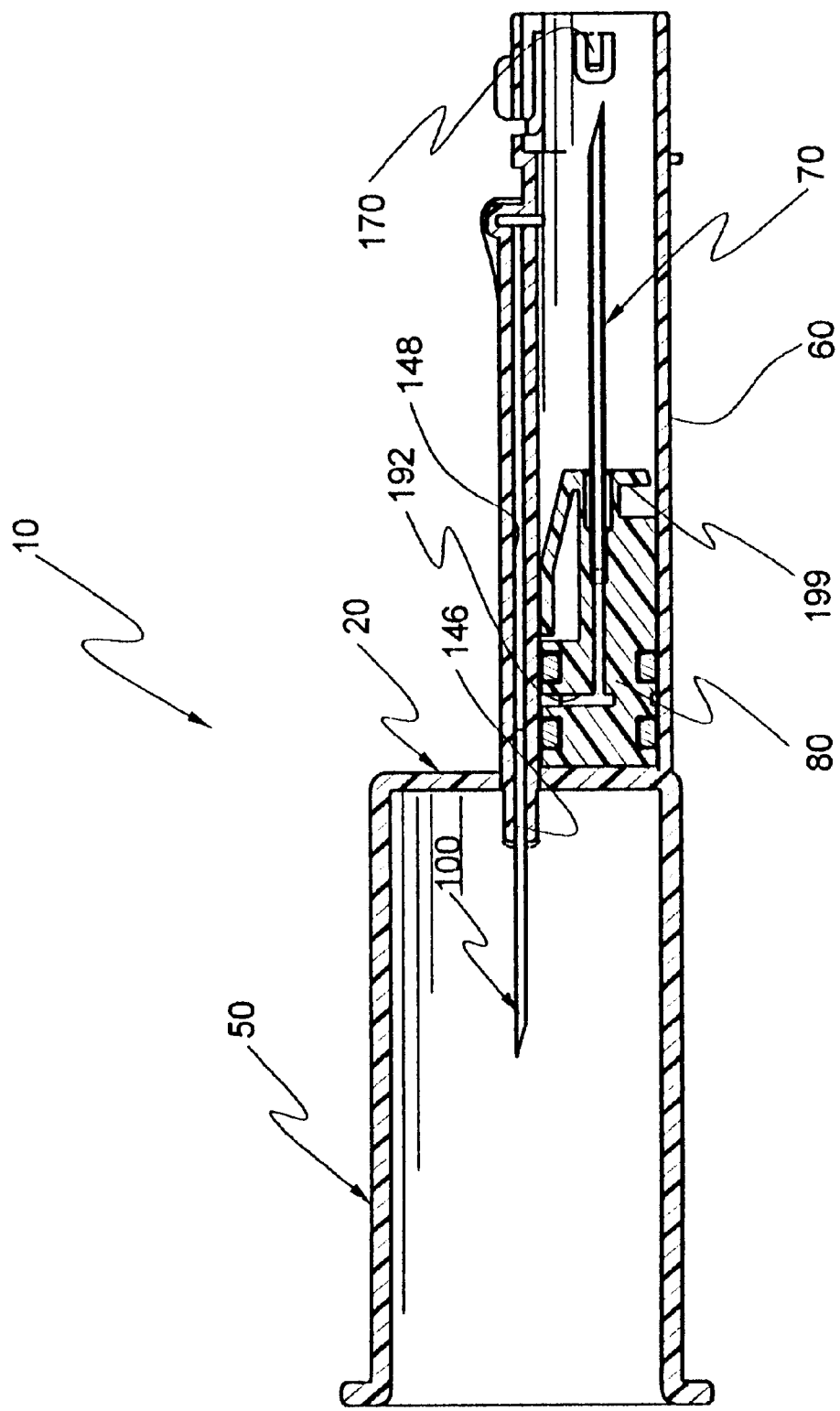
FIG. 10 is a section of the device seen in FIG. 9 with the medical needle retracted for safety into the housing.

Needle 70 is seen retracted into safety of housing 20) in FIG. 10. As there is no simple way to reengage hook 206 into slot 199, without extraordinary measures, device 10 can only be used once.

Figure 11:
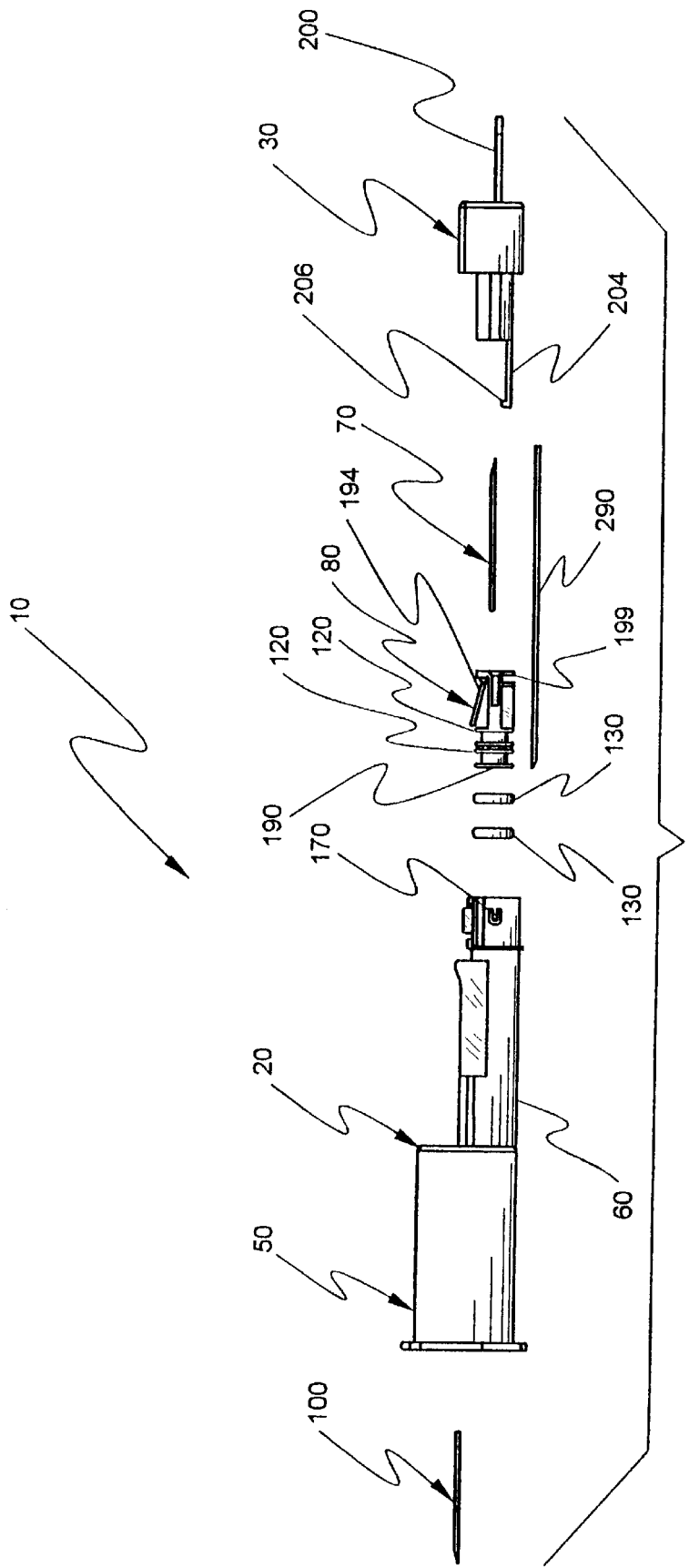
FIG. 11 is an exploded side elevation of device parts and a rod used in device assembly.

Referring to FIG. 11, assembly of device 10 comprises a series of linear actions. One o-ring 130 is disposed into each groove 120. Needle 70 is securely affixed into hub 80, and needle 100 is likewise affixed into hub 230 (seen in FIG. 8) of proximal barrel portion 50. Hook 206 of cap 30 is deployed into slot 199. A long thin rod, such as rod 290 is inserted along inner surface 250 of distal section 60. Of course, a sealable air evacuation hole (not shown), proximally disposed in section 60, may be used instead of rod 290. Latch leg 194 is depressed to permit passage of leg 194 across catch ledge 260 and the assembly comprising hub 80, needle 70 and cap 30 are inserted into distal section 60. The presence of rod 290 permits air to escape during insertion. Once proximal end 190 is fully seated, rod 290 is withdrawn, and tab 170 is permanently distorted to form a stop against pulling hub 80 from distal section 60. Such distortion of plastic parts is well known in the plastics forming art. As an example, polypropylene is commonly warmed to a predetermined temperature and permanently distorted. A label 40 (not seen in FIG. 11) is affixed to rim 142 and cap 30 is affixed to secure device 10 for transport. Cap 30 is preferably affixed by heat staking a portion of section 202 to section 60. Heat staking is commonly used to releasibly couple plastic parts. So configured, device 10 may be sterilized and shipped to a point of use without further packaging, if desired.

Figure 12:
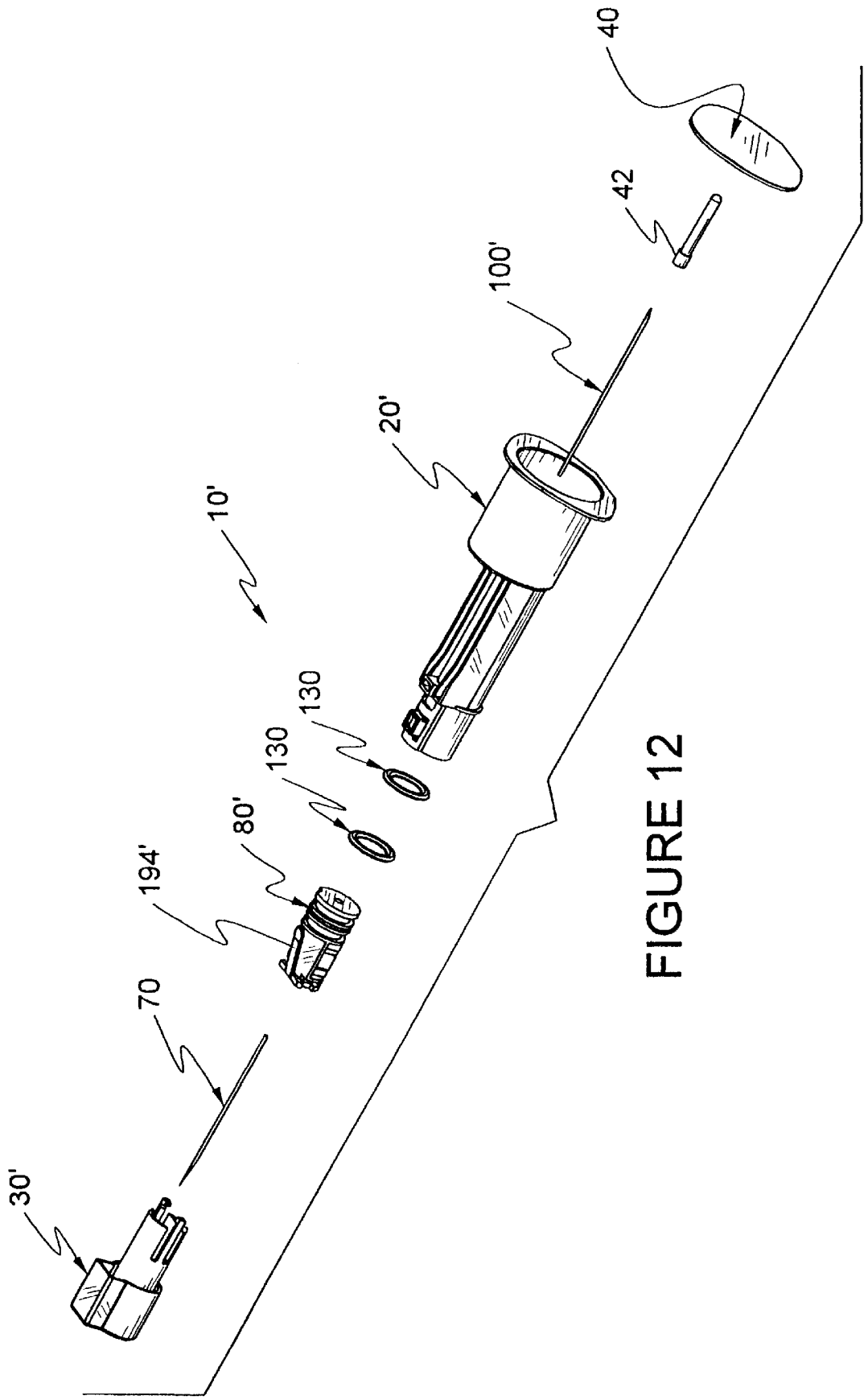
FIG. 12 is an exploded view of parts used in a second embodiment of the present invention.

Another embodiment of the invention, device 10', is seen in FIGS. 12-15 and 17. As seen in FIG. 12, device 113' comprises a cap 30', a distal medical needle 70, hub 80', a pair of o-rings 130, a housing 20', a proximal needle 100', a blood valve 42 and a label 40. As in device 10, device 10' requires but three injection molded parts, in this case, cap 30', housing 20' and hub 80'. Major differences between parts of device 10 and parts of device 10' are found in cap 3, hub 80', housing 20' and proximal needle 100'. As the overall form and function of device 10' are similar in most ways to that of device 10, only differences between parts of the two devices are disclosed hereafter.

Figure 13:
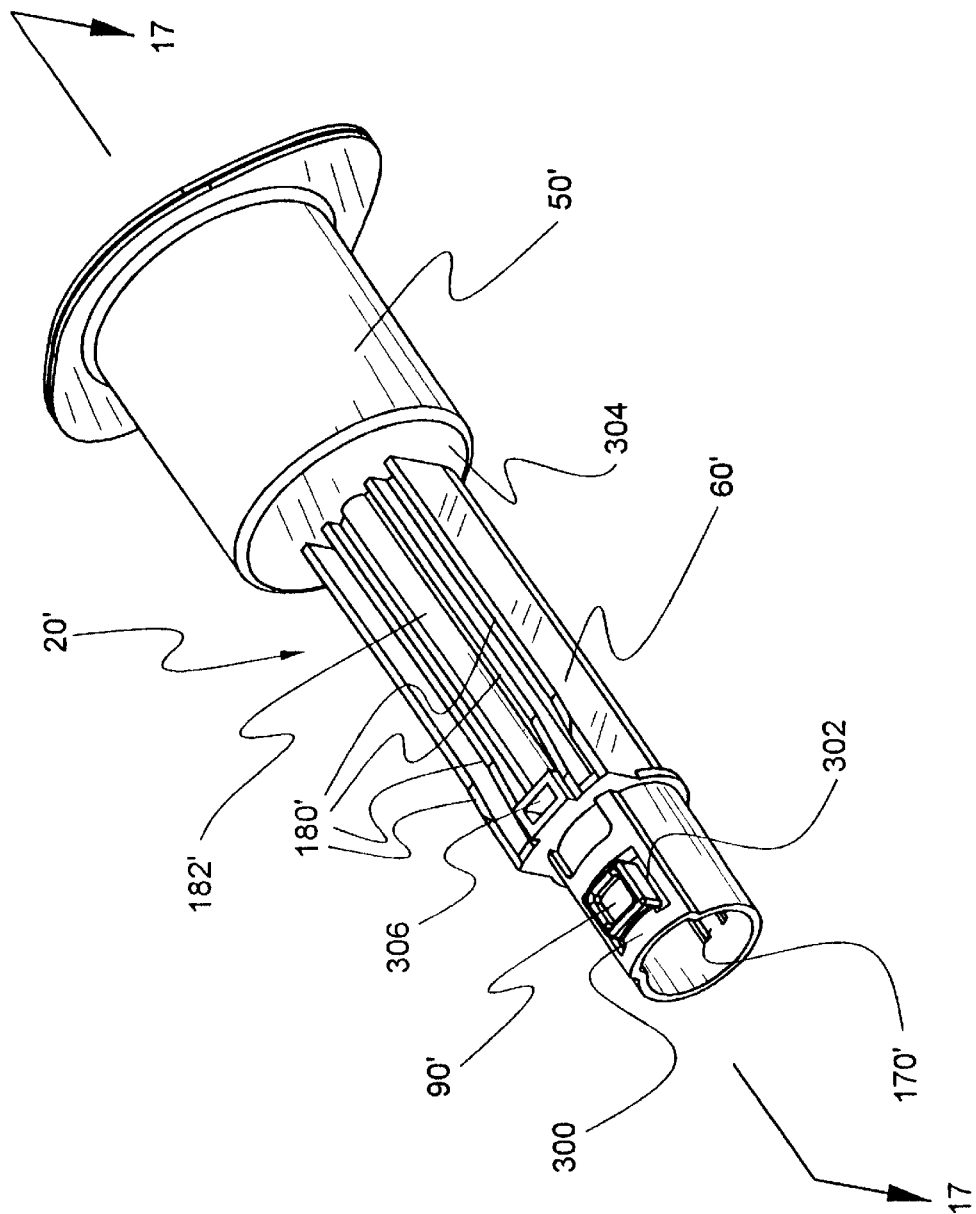
FIG. 13 is a perspective of a housing part of the second embodiment.

An enlarged barrel 20' is seen in FIG. 13. While proximal barrel portion 50' and distal section 60' are similar in appearance and function, at least section 60' comprises some remarkable differences when compared to section 60. Notice that device 20' comprises but one tab 170' which acts as a guide when removing cap 30'. Button 90' has a cantilevered attachment 300 to the rest of section 60' and comprises a raised rectangular segment 302 for depressive access to a trigger leg 194'. Ribs 180' extend to a distal face 304 of barrel portion 304, such extending of ribs 180' may be used for reducing general barrel distortion from the molding process. Material 182' covers a conduit 148' which is described in more detail hereafter. An open duct 306 provides molding access to a distal end of conduit 148'. As is true of tabs 170, tab 170' is inwardly deformed after needle 70, hub 80' and cap 30' are in place to form a guide as previously mentioned and a stop to prevent hub 80' from being pulled from section 60' as needle 70 is extended by removal of cap 30'.

Figure 14:
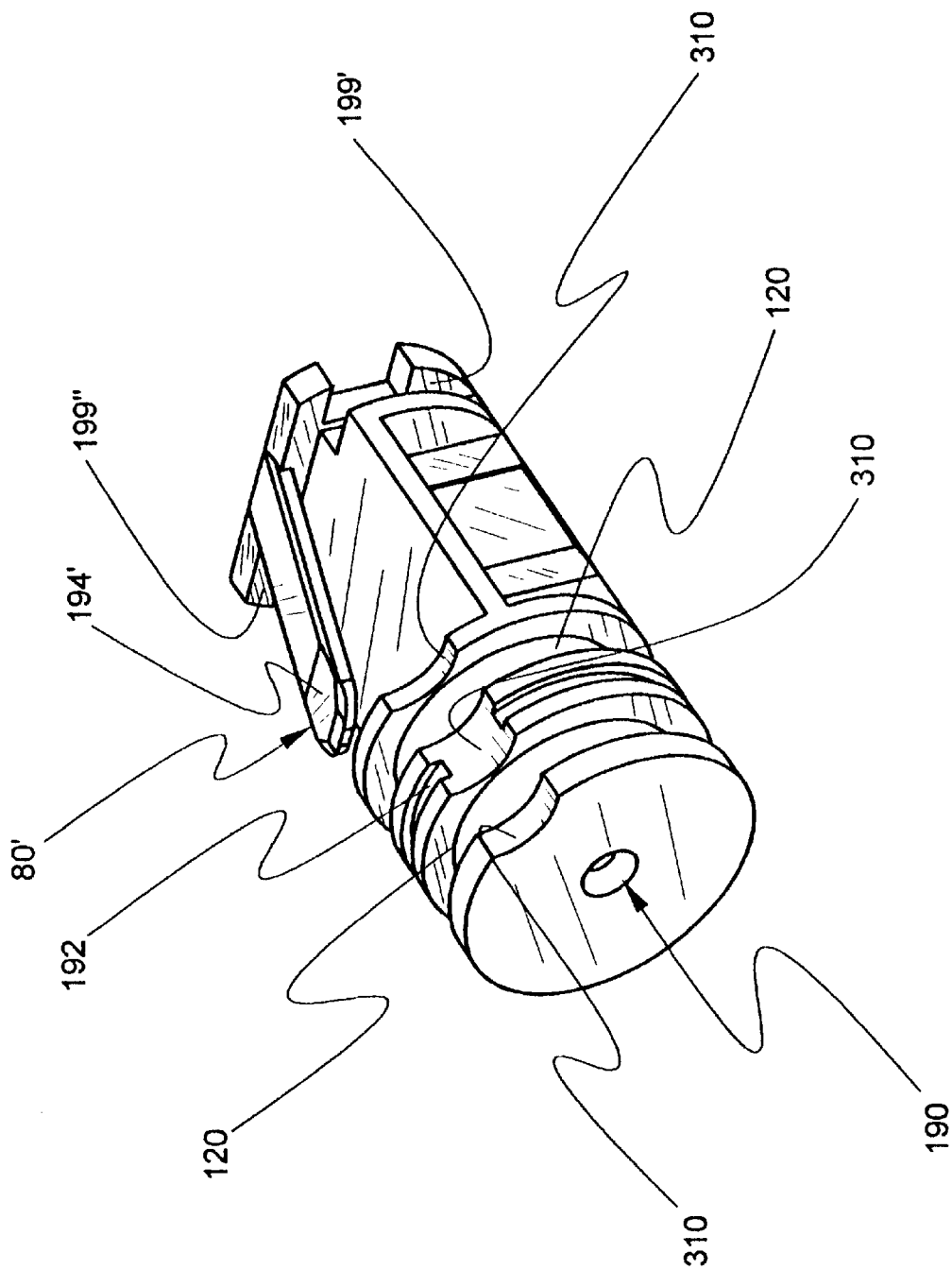
FIG. 14 is a perspective of a needle hub, which is a part of the second embodiment.

A perspective of hub 80' is seen in FIG. 14. Hub 80' is similar to hub 80, seen in FIG. 6, but comprises a pair of pull slots 199' and 199" vertically disposed on opposite sides of hub 80'. A pair of hooks 206' and 206" are disposed to be releasibly affixed in respective slots 199' and 199" of hub 80' to provide a more balanced pull than that of the hub 80 and cap 30 interface. A single inferiorly disposed guide slot 222' provides a controlled linear extension as cap 30' is removed from section 60'. Similar to hub 80, hub 80' comprises a slot 192, a pair of o-ring grooves 120 disposed about slot 192, a closed end 190 and trigger leg 194'. Hub 80' also comprises a series of indentations, generally numbered 310, whereby a gas releasing rod 290 (see FIG. 11) may be disposed within section 60' as hub 80' is inserted into section 60'.

Figure 15:
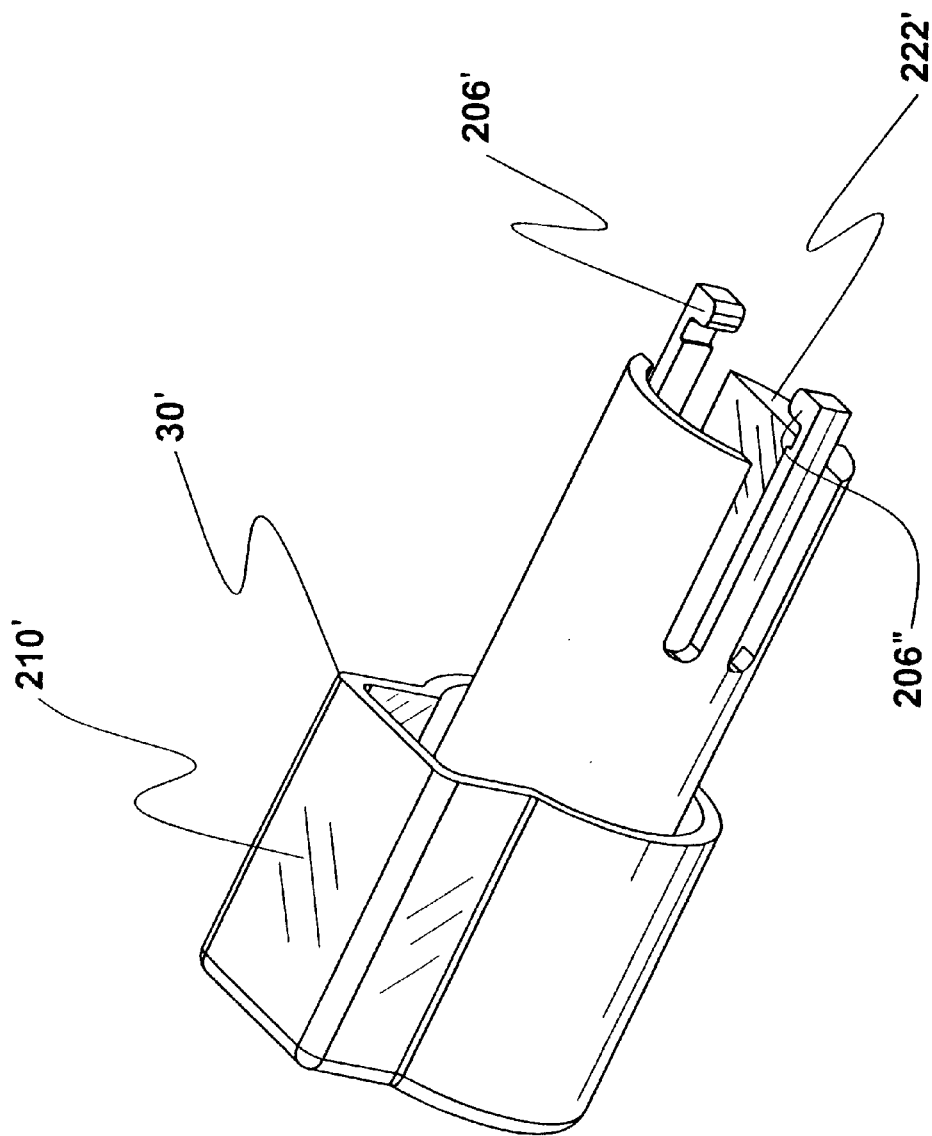
FIG. 15 is a perspective of a cap, which is a part of the second embodiment.

Referring to FIG. 15, note that pull tab 200 is not a part of cap 30'. While a tab, such as tab 200, may be added to cap 30', using distal cover 210' as a puller, permits shortening of device 10' relative to device 10.

Figure 17:
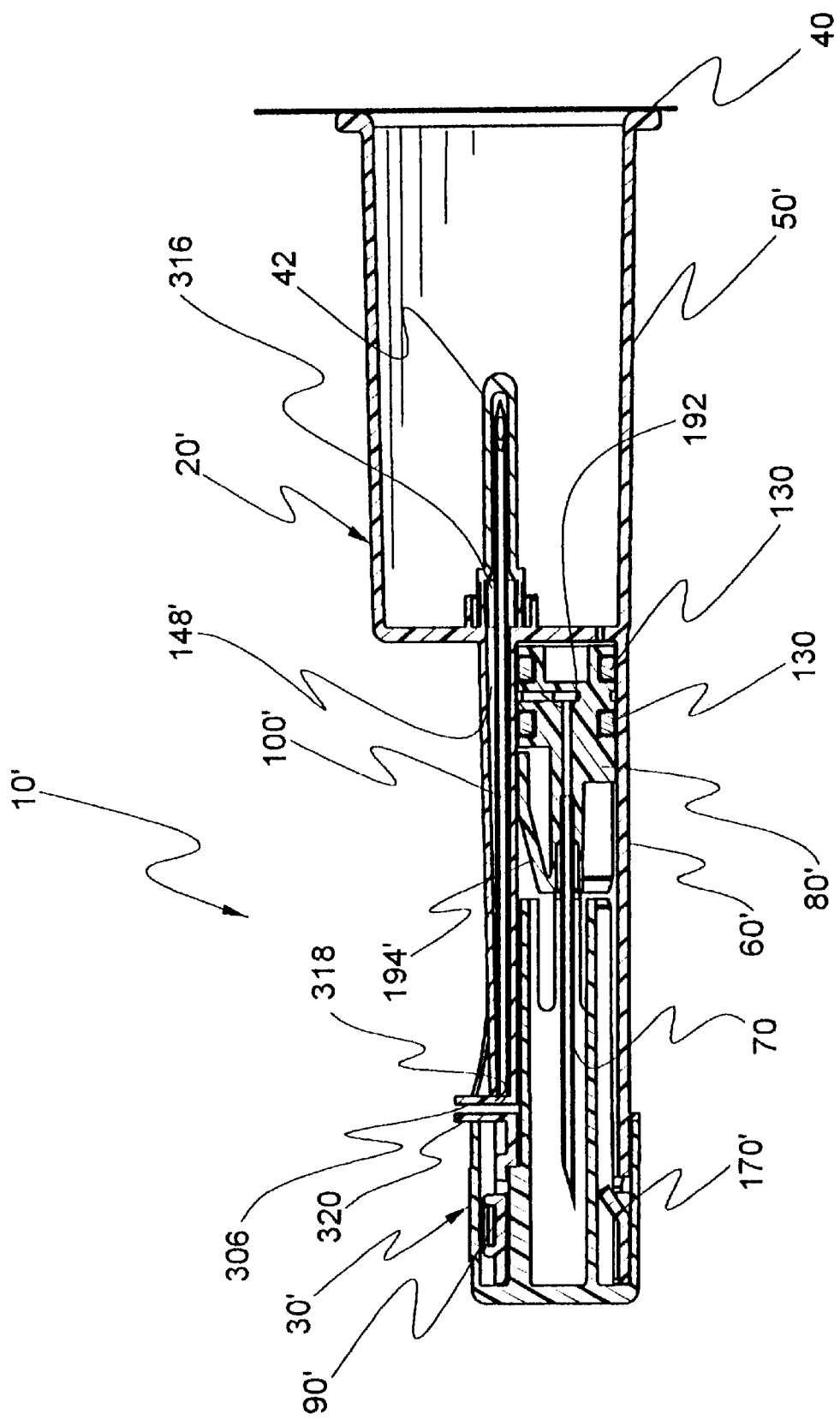
FIG. 17 is a section along lines 17—17 of FIG. 13, after the label has been removed and before cap is removed and showing parts including cap and needle in place before hub and needle extension.

Reference is now made to FIG. 17 wherein proximal needle 100', which is significantly longer than needle 100, is seen to extend through most of conduit 148'. As seen in FIG. 17, conduit 148' comprises a hollow, frustoconical shape, having a proximally disposed larger diameter orifice 316 and a distally disposed smaller diameter orifice 318 which communicates with open duct 306. Draft resulting from the different sized diameters 316 and 318 permit simpler mold design and release techniques to be used than that which is required to mold conduit 148 while attaining a small integral dead space. A secure seal is made between needle 100' and conduit 148' near orifice 318 by adhesive or other material or method commonly used to affix hollow bore needles within channels formed in synthetic resinous material. In this manner, dead space along conduit 148' is limited to the inner volume of the hollow bore of needle 100'.

Of course, as earlier noted, the pathway defined from needle 70 through duct 306, orifice 318 and needle 100' must be otherwise closed. To accomplish this, a wall 320 which surrounds a superior portion of duct 306 is closed, preferably by heat deformation, also preferably at the same time tab 170' is deformably inwardly depressed, thereby forming tab 170' as a guide and stop for hub 80'.

Figure 16:
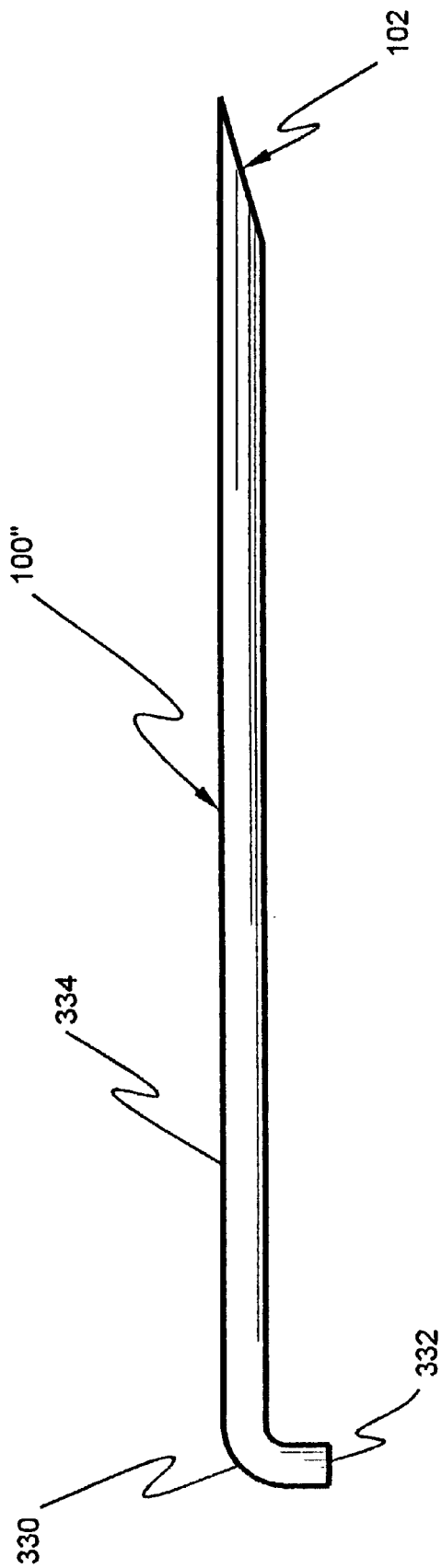
FIG. 16 is a side elevation of a rear phlebotomy needle having a right angle bend in the end distal to the pointed end of the needle.

An alternative embodiment to ducts 148 and 148' may be provided by providing a first entry connection (not shown in place of a superior portion of duct 306 and a second entry connection (not shown) at orifice 316 for a connecting tube. Such a tube, numbered 100" is seen in FIG. 16. Note that tube 100" comprises a right angle bend 330 and an inferiorly disposed blunt end 332 for connecting to a remaining inferior portion of duct 306. The proximally disposed portion 334 of needle 100" comprises an elongated hollow bore member which terminates in a needle point at an end 102, which is like end 102 seen in FIG. 8.

The invention disclosed herein may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by letters patent is:

What is claimed is:

1. A barrel part for use in an extendable and retractable safety medical needle device, said barrel part comprising:

a hollow, cylindrically shaped proximal part comprising a first elongated sidewall, a proximally disposed opening for receiving fluid sampling tubes and a substantially closed distal end comprising a hub having a centrally disposed bore hole wherein a proximally directed sharpened cannula is disposed to provide a communicating pathway into each sampling tube inserted into said proximal part and perforated by said sharpened cannula;

an elongated hollow, tubular portion comprising:

a closed proximal end which forms a wall which is contiguous with said distal closed end; and a second elongated sidewall having a hollow cylindrical shape for a plunger which when drawn away from said closed proximal end evacuates and essentially produces a vacuum within a volume defined by the closed proximal end, a portion of the second sidewall and the plunger and a fluid communicating passageway from the plunger to said communicating pathway, said passageway comprising a fluid flow path which is separate and independent from the volume.

2. A barrel part according to claim 1 wherein said second sidewall comprises an internal surface having a catch for a latching part disposed therein.

3. A barrel part according to claim 1 wherein said second sidewall comprises an elongated channel which forms a part of said passageway.

4. A barrel part according to claim 1 wherein said distal portion comprises a tab which restricts removal of the plunger from the tubular portion in which the plunger is disposed.

5. An extendable and retractable safety phlebotomy device comprising:

a housing comprising a proximal hollow, elongated cylindrical portion and a distal hollow, elongated tubular portion;

said proximal portion comprising an open proximal end for receiving fluid sampling tubes and a distal end closed about a needle hub;

a cannula, having a proximally directed sharpened tip, securely affixed in said needle hub and providing a fluid pathway therethrough;

said distal portion comprising a closed proximal end in the form of a wall common with a portion of said distal end, an elongated sidewall defining an interior tubular surface and a distally disposed opening;

a displaceable needle assembly comprising a hub for a medical needle, a hollow medical needle, an energy storing element and a plunger comprising a slidable part having at least two seals defining a blood flow path therebetween and being disposed about said hub and aligned transverse to the interior tubular surface, the needle assembly being disposed within the distal portion prior to use, partially advanced through said distal opening to extend the medical needle for use in a medical procedure and retracted by force generated by conversion of stored energy, created by displacing at least one of the seal parts away from the proximal closed end along the interior tubular surface and stored in the energy storing element, to safely secure the medical needle inside the distal portion after use;

the hub further comprising a releasible latch and the distal portion comprising a catch whereby the needle assembly is releasibly affixed when displaced for the procedure;

said sidewall comprising a closed conduit having an opening at a proximal end which communicates with said fluid pathway and having an opening at a predetermined distal site through said sidewall;

said hub having a fluid communicating recess which delivers fluid from a proximal end of said medical needle into the hollow of said distal portion; and said at least two seal parts being disposed about said slot and also disposed to provide a sealed pathway from said recess to said site when the needle assembly is displaced for use in the medical procedure.

6. An extendable and retractable safety Phlebotomy device according to claim 5 wherein said at least two seal parts and said distal portion, in combination, form the energy storing element by drawing a vacuum as the needle is displaced distally.

7. An extendable and retractable safety Phlebotomy device according to claim 5 wherein said energy storing element is an elastic member.

8. An extendable and retractable safety Phlebotomy device according to claim 5 wherein said energy storing element is a spring.

9. An extendable and retractable safety phlebotomy device according to claim 5 further comprising a removable label which closes and seals the open proximal end and provides evidence of tampering when removed.

10. An extendable and retractable safety phlebotomy device according to claim 5 further comprising a cap which provides a sterile barrier and denies access to the medical needle until removed.

11. An extendable and retractable safety phlebotomy device according to claim 5 wherein the hub comprises a catch and the device further comprises a cap comprising a releasable fastener which hooks to said hub catch to draw the needle assembly outward from the distal portion as the cap is removed from the device.

12. An extendable and retractable safety phlebotomy device according to claim 5 wherein said interior surface comprises rails and the cap comprises grooves which are complementary with the rails to assure linear extension of said needle as the fastener is pulled from the distal portion,.

13. An extendable and retractable safety phlebotomy device according to claim 5 wherein said seal parts communicate with said side wall to provide closure at the proximal end of said medical needle when said sealed pathway is disjoined as the hub is retracted.

14. An extendable and retractable safety phlebotomy device comprising:

a housing comprising a proximal hollow, elongated cylindrical portion and a distal hollow, elongated tubular portion;

said proximal portion comprising an open proximal end for receiving fluid sampling tubes and a distal end closed about a needle hub;

a cannula, having a proximally directed sharpened tip, securely affixed in said needle hub and providing a fluid pathway therethrough;

said distal portion comprising a closed proximal end in the form of a wall common with a portion of said distal end, an elongated sidewall defining an interior tubular surface and a distally disposed opening;

a displaceable needle assembly comprising a hub for a medical needle, a hollow medical needle, and a plunger comprising at least two slidable seal parts disposed about said hub and aligned transverse to the interior tubular surface, the needle assembly being disposed within the distal portion prior to use, partially advanced through said distal opening to extend the medical needle for use in a medical procedure and retracted by force of vacuum, created by displacing at least one of the seal parts away from the proximal closed end along the interior tubular surface, to safely secure the medical needle inside the distal portion after use;

the hub further comprising a releasible latch and the distal portion comprising a catch whereby the needle assembly is releasibly affixed when displaced for the procedure;

said sidewall comprising a closed conduit having an opening at a proximal end which communicates with said fluid pathway and having an opening at a predetermined distal site through said sidewall;

said hub having a fluid communicating recess which delivers fluid from a proximal end of said medical needle into the hollow of said distal portion; and said at least two seal parts being disposed about said slot and also disposed to provide a sealed pathway from said recess to said site when the needle assembly is displaced for use in the medical procedure.

15. An extendable and retractable safety phlebotomy device according to claim 14 further comprising a removable label which closes and seals the open proximal end and provides evidence of tampering when removed.

16. An extendable and retractable safety phlebotomy device according to claim 14 further comprising a cap which provides a sterile barrier and denies access to the medical needle until removed.

17. An extendable and retractable safety phlebotomy device according to claim 14 wherein the hub comprises a catch and the device further comprises a cap comprising a releasible fastener which hooks to said hub catch to draw the needle assembly outward from the distal portion as the cap is removed from the device.

18. An extendable and retractable safety phlebotomy device according to claim 14 wherein said interior surface comprises rails and the cap comprises grooves which are complementary with the rails to assure linear extension of said needle as the fastener is pulled from the distal portion.

19. An extendable and retractable safety phlebotomy device according to claim 14 wherein said seal parts communicate with said side wall to provide closure at the proximal end of said medical needle when said sealed pathway is disjoined as the hub is retracted.

20. A safety phlebotomy device comprising;

a housing comprising a proximally disposed portion, having a hollow cylindrical core which is closed at a distal end except for a needle hub and associated through hole which provides for fluid communication therethrough, and a distally disposed portion having a hollow elongated tubular shape and being closed at a proximal end which is integral with the distal end of the proximally disposed portion;

an extendable and retractable medical needle assembly comprising a hollow medical needle which is at least partially disposed in said distally disposed tubular portion and protected by a releasible cover during transport, extended from said housing during use in a medical procedure and retracted for safety into said housing after use;

said medical needle assembly further comprising a slideable seal assembly which acts as a plunger which draws a vacuum in a space within the distally disposed tubular portion when said assembly is displaced to extend said needle for use, said housing and said medical needle assembly cooperatively providing a fluid path, from said medical needle into said hollow core, which is separate from the space within the distally disposed tubular portion in which the vacuum is drawn.

21. A safety phlebotomy device according to claim 20, wherein said distally disposed tubular portion comprises a catch and said medical needle assembly comprises a corresponding releasible latch whereby said assembly is releasibly latched when said needle is extended.

22. A safety phlebotomy device according to claim 20, wherein said distally disposed tubular portion comprises a sidewall having a channel disposed therein which is a segment of the fluid path.

23. A safety phlebotomy device according to claim 20, wherein said distally disposed tubular portion comprises a latch release which is manually actuated to release the latch from the catch permitting energy stored via said vacuum to retract the needle and needle assembly into the distally disposed tubular portion.

24. A safety phlebotomy device according to claim 23, wherein said latch release comprises a cantilevered button integral to said housing.

* * * * *